(12) United States Patent
Lian et al.

(10) Patent No.: US 12,420,274 B2
(45) Date of Patent: Sep. 23, 2025

(54) METHOD FOR TREATING OR REGENERATING METAL CATALYST AND APPLICATION

(71) Applicant: BEIJING SINGLE ATOM SITE CATALYSIS TECHNOLOGY CO., LTD, Beijing (CN)

(72) Inventors: Chao Lian, Beijing (CN); Yang Li, Beijing (CN); Jianxing Shi, Beijing (CN); Mengyun Wang, Beijing (CN); Hongchen Yang, Beijing (CN); Mingliang Deng, Beijing (CN); Minduo Wang, Beijing (CN)

(73) Assignee: BEIJING SINGLE ATOM SITE CATALYSIS TECHNOLOGY CO., LTD, Beijing (CN)

( * ) Notice: Subject to any disclaimer, the term of this patent is extended or adjusted under 35 U.S.C. 154(b) by 277 days.

(21) Appl. No.: 18/259,970

(22) PCT Filed: Dec. 21, 2021

(86) PCT No.: PCT/CN2021/139865
§ 371 (c)(1),
(2) Date: Jun. 29, 2023

(87) PCT Pub. No.: WO2022/143275
PCT Pub. Date: Jul. 7, 2022

(65) Prior Publication Data
US 2024/0091760 A1    Mar. 21, 2024

(30) Foreign Application Priority Data

Dec. 31, 2020   (CN) .......................... 202011637274.3
Apr. 1, 2021    (CN) .......................... 202110354097.6

(51) Int. Cl.
*B01J 38/08*   (2006.01)
*B01J 21/04*   (2006.01)
(Continued)

(52) U.S. Cl.
CPC ............ *B01J 38/08* (2013.01); *B01J 21/04* (2013.01); *B01J 21/08* (2013.01); *B01J 23/10* (2013.01);
(Continued)

(58) Field of Classification Search
CPC ............ B01J 38/08; B01J 21/04; B01J 21/08; B01J 23/10; B01J 23/26; B01J 23/34;
(Continued)

(56) References Cited

U.S. PATENT DOCUMENTS

2003/0044348 A1    3/2003    Sato et al.
2004/0266612 A1*  12/2004   Hayes .................. C07C 5/02
                                                        502/240
(Continued)

FOREIGN PATENT DOCUMENTS

CN    103769156    5/2014
CN    104588007    5/2016
(Continued)

OTHER PUBLICATIONS

International Search Report received in the parent International Patent Application No. PCT/CN2021/139865, dated Mar. 21, 2022, 2 pages.

*Primary Examiner* — Ellen M McAvoy
(74) *Attorney, Agent, or Firm* — Kilpatrick Townsend & Stockton LLP

(57) ABSTRACT

The present invention relates to a method for preparing, activating and regenerating a metal supported catalyst, comprising: treating a $M_a$-$M_b$-$M_c$ metal supported catalyst at 10-700° C. by using an ammonia or nitrogen-containing (Continued)

organic matter, wherein the $M_a$ metal is an active metal selected from one or more of a noble metal atom or a transition metal, the support is a common industrial porous catalyst, and the $M_a$ metal is dispersed on the support in a state of single atomic site. According to the $M_a$-$M_b$-$M_c$ metal supported noble metal/zinc catalyst treated by the method of the present invention, the direct dehydrogenation conversion rate and selectivity of catalyzing light alkanes are remarkably improved; the method for preparing the catalyst is simple in process, the catalytic activity after regeneration is still kept, and the catalyst can be industrially produced on a large scale.

19 Claims, 1 Drawing Sheet

(51) Int. Cl.
| | |
|---|---|
| *B01J 21/08* | (2006.01) |
| *B01J 23/10* | (2006.01) |
| *B01J 23/26* | (2006.01) |
| *B01J 23/34* | (2006.01) |
| *B01J 23/60* | (2006.01) |
| *B01J 23/80* | (2006.01) |
| *B01J 23/89* | (2006.01) |
| *B01J 29/74* | (2006.01) |
| *B01J 37/02* | (2006.01) |
| *B01J 37/08* | (2006.01) |
| *B01J 37/18* | (2006.01) |
| *B01J 38/02* | (2006.01) |
| *B01J 38/10* | (2006.01) |
| *B01J 38/12* | (2006.01) |
| *C07C 5/32* | (2006.01) |

(52) U.S. Cl.
CPC ............... *B01J 23/26* (2013.01); *B01J 23/34* (2013.01); *B01J 23/60* (2013.01); *B01J 23/80* (2013.01); *B01J 23/8913* (2013.01); *B01J 23/8953* (2013.01); *B01J 29/74* (2013.01); *B01J 37/0201* (2013.01); *B01J 37/082* (2013.01); *B01J 37/18* (2013.01); *B01J 38/02* (2013.01); *B01J 38/10* (2013.01); *B01J 38/12* (2013.01); *C07C 5/325* (2013.01); *C07C 2523/10* (2013.01); *C07C 2523/24* (2013.01); *C07C 2523/60* (2013.01); *C07C 2523/80* (2013.01)

(58) Field of Classification Search
CPC ........ B01J 23/60; B01J 23/80; B01J 23/8913; B01J 23/8953; B01J 29/74; B01J 37/18; B01J 38/02
See application file for complete search history.

(56) References Cited

U.S. PATENT DOCUMENTS

| | | | | |
|---|---|---|---|---|
| 2008/0207437 | A1* | 8/2008 | Mabilon | B01J 37/0205 585/700 |
| 2010/0168493 | A1* | 7/2010 | Le Peltier | C10G 35/09 585/660 |
| 2017/0120222 | A1* | 5/2017 | Kim | B01J 37/036 |
| 2017/0354962 | A1* | 12/2017 | D'Souza | B01J 37/0203 |
| 2019/0262821 | A1* | 8/2019 | Doosa | B01J 35/633 |
| 2020/0122122 | A1* | 4/2020 | Gong | B01J 29/043 |
| 2021/0154654 | A1* | 5/2021 | Boualleg | B01J 37/0205 |
| 2021/0354116 | A1* | 11/2021 | Stobbe | B01J 27/0576 |
| 2022/0219150 | A1* | 7/2022 | Li | B01J 23/44 |
| 2023/0127784 | A1* | 4/2023 | Park | B01J 23/96 423/628 |

FOREIGN PATENT DOCUMENTS

| | | |
|---|---|---|
| CN | 105921148 | 9/2016 |
| CN | 106607105 | 5/2017 |
| CN | 107661763 | 2/2018 |
| CN | 107661767 | 2/2018 |
| CN | 109225306 | 1/2019 |
| CN | 109701588 | 5/2019 |
| CN | 111215053 | 6/2020 |
| CN | 111495378 | 8/2020 |
| WO | 2020078980 A1 | 4/2020 |

* cited by examiner

METHOD FOR TREATING OR REGENERATING METAL CATALYST AND APPLICATION

TECHNICAL FIELD

The present invention belongs to the petrochemical technical field, specifically relates to catalyst for the dehydrogenation of alkane.

BACKGROUND OF THIS INVENTION

Light olefins are basic raw materials in petrochemical industry, which are widely used in the production of organic chemical raw materials, resins, rubbers, plastics, synthetic gasoline and so on. In the past, light olefins were mainly obtained from by-products of fluid catalytic cracking (FCC) units in the petroleum industry. In recent years, the gap between the global demand for light olefins and the product capacity of traditional sources has been continually increasing. In China, for instance, the domestic consumption of propylene in 2015 was 30.4 million tons, in which 2.76 million tons relied on imports. With the increasingly mature technology of dehydrogenation of shale gas to produce light olefins in the United States, the cost of dehydrogenation of light alkane is obviously reduced. The production process of dehydrogenation of light alkane has been widely applied due to the large supply gap and the increasing price of light olefins in China.

At present, the most widely used light alkane dehydrogenation processes in the world are Oleflex process of UOP and Catofin process of Lummus Catofin process uses Cr-base catalyst with alumina as support and chromic oxide as active component. The catalytic dehydrogenation of Catofin process is carried out in fixed bed reactor. The advantages of Catofin process are low cost of catalyst and high conversion of alkane, while its disadvantages are short duration of catalytic reaction, rapid coke deposition on the surface of catalyst during the reaction process, and frequent switching between regeneration and catalysis processes. In addition, chromium compounds have high toxicity and are easy to cause environmental pollution.

Oleflex process uses Pt-base catalyst with alumina as support, noble metal platinum as active component, and tin and alkali metals as promoters. The catalytic dehydrogenation is carried out in moving bed reactor. The advantages of Oleflex process are longer lifetime of the catalyst and less environmental pollution, while its disadvantage is higher cost of the catalyst.

In recent years, single-atom catalyst has received widespread attention. The active components of the catalyst exist in the form of single atoms and have the highest atomic utilization rate, which can extremely reduce the amount of active components used. In the reported single-atom catalysts, CN modified noble metal single-atom catalyst exhibited huge practical application potential due to the stability and modification effect of N on single-atom of metal in CN materials (Adv. Mater, 2019, 31, 1901024; Nano Res., 2019, 12, 2584; Nat. Nanotech., 2020, 15, 390; CN109225306A). However, the dehydrogenation reaction of light alkane always exists serious coking problems, which need continuous burning coke and regeneration treatment to the catalyst. CN modified noble metal single atom catalyst often has defects such as complex preparation process and difficulty in industrial regeneration after catalyst coking, which hinder the further industrial promotion.

CONTENTS OF INVENTION

Firstly, this invention provides a method I for treating metallic catalyst comprises: treating metal supported catalyst with ammonia or nitrogen-containing organic, the metal supported catalyst is a $M_a$-$M_b$-$M_c$ metal supported catalyst, wherein $M_a$ is active metal which is selected from one or more of noble metal or transition metal, wherein the noble metal is selected from one or more mixtures of Pt, Au, Ru, Rh, Pd, Ir and Ag, the transition metal is selected from La, Fe, Co, Mn, Cr, Ni or Cu, the content of $M_a$ is 0.01-5 wt % based on catalyst weight; $M_b$ metal is selected from one or more combinations of Zn, Sn, Co and Al, the content of $M_b$ is 0.1-20 wt % based on catalyst weight; $M_c$ is selected from K, Na and the mixture thereof, the content of $M_c$ is 0-20 wt % based on catalyst weight; the support comprises alumina, silica-alumina, zirconia, cerium oxide, titanium oxide, or molecular sieves or the mixture thereof.

Optionally, the metal supported catalyst does not contain $M_c$ metal as the form of $M_a$-$M_b$. The method comprises: treating metal supported catalyst with ammonia or nitrogen-containing organic at 10° C.-700° C.

$M_a$ is active metal which is selected from one or more of noble metal and transition metal, wherein the noble metal is selected from one or more mixtures of Pt, Au, Ru, Rh, Pd, Ir and Ag, the transition metal is selected from La, Fe, Co, Mn, Cr, Ni and Cu, preferably the active metal is Pt, Ru, Pd, Ir, Cr, Ni, PtPd, IrPt, IrPd, or IrPtPd. $M_b$ metal is selected from one or more combinations of Zn, Co and Al, preferably Zn, Co or Zn—Co mixed metal.

The supports are commonly used catalyst supports in industry which comprise alumina, silica-alumina, zirconia, cerium oxide, titanium oxide, or molecular sieves or the mixture containing any two or more of them; the catalyst support functions as a carrier. The shape of the supports is selected from non-formed powder, or shaped structure, the shaped structure is selected from spherical shape, strip shape, cylindrical shape, shape with multi-porous channels, honeycomb shape and so on. γ-alumina, titanium oxide, silica, NaY molecular sieve supports have been carried out in this invention.

The $M_a$ metal is loaded on the support in a state of single-atom sites, or in a state of coexistence of single-atom sites, with clusters and/or nanoparticles, specifically in the state of single-atom sites, or in the state of coexistence of single-atom sites and clusters, or in the state of coexistence of single-atom sites, clusters and nanoparticles. The content of $M_a$ is 0.01-5 wt %, preferably 0.05-2 wt % based on catalyst weight; the content of $M_b$ is 0.1-20 wt %, preferably 0.1-10 wt %, especially preferably 0.5-4 wt % based on catalyst weight, the content of $M_c$ is 0%.

To obtain the $M_a$-$M_b$ metal supported catalysts, a $M_a$ metal precursor and a $M_b$ precursor are loaded on the support according to the designed amount to prepare a catalyst precursor. The method for loading comprises common method in this field, such as impregnation, rotary evaporation, adsorption, ion exchange, incipient wetness, precipitation, spray drying. The examples in this invention used impregnation method and rotary evaporation method for loading.

The loading of $M_a$ and $M_b$ metal can be carried out simultaneously or sequentially. The $M_a$ metal precursor is soluble $M_a$ metal inorganic salt, organic salt in solvent or metal complex, preferably nitrate, chloride, sulphate, acetate, acetylacetone salt, complex; the $M_b$ metal precursor is soluble organic or inorganic salt in solvent of $M_b$, preferably nitrate, chloride, sulphate, acetate, oxalate, acetylacetone salt, such as zinc nitrate, cobalt nitrate, zinc chloride, cobalt chloride, zinc acetate, cobalt acetate and so on. The solvent is water or alcohol, wherein the alcohol is methanol or ethanol.

The ammonia comprises ammonia gas or substance that can release ammonia, wherein substance that can release ammonia comprises urea, ammonium nitrate, hexamethylenetetramine or ammonium nitrate; optionally, the substance and the catalyst are placed in the same room, the substance releases $NH_3$ by heating or adding alkali, and the $NH_3$ interacts with catalyst.

The nitrogen-containing organic is selected from $C_{1-6}$ alkyl amine, $C_{2-6}$ alkenyl amine, $C_{6-20}$ aryl amine, $C_{4-20}$ cyclic alkyl amine, $C_{4-20}$ nitrogen-containing heterocyclic ring, $C_{4-20}$ nitrogen-containing heteroaromatic ring and $(RCO)_xNR_{3-x}$, wherein R is H or $C_{1-6}$ alkyl, x is 1 or 2; the amine is a monamine or polyamin; preferably, the alkyl, alkenyl, aryl, nitrogen-containing heterocycle ring and nitrogen-containing heteroaromatic ring are independently further substituted by oxygen, carbonyl, carboxyl, ester group, or amino group; the aryl is monocyclic aryl or fused polycyclic aryl; the nitrogen-containing heterocyclic ring is a monocyclic or fused non-aromatic ring containing cyclic nitrogen atom, and a cyclic carbon is optionally replaced by oxygen; the nitrogen-containing heteroaromatic ring is a monocyclic or fused polycyclic heteroaromatic ring containing cyclic nitrogen atom, and a cyclic carbon is optionally replaced by oxygen; the nitrogen-containing organic is preferably $C_{1-6}$ alkyl amine, $C_{1-6}$ alkyl diamine, $C_{6-20}$ aryl amine, dimethyl formamide; The nitrogen-containing organic specifically carried out in the invention is ethylenediamine, triethylamine, butylamine, aniline or dimethyl formamide; preferably ethylenediamine.

The ammonia or nitrogen-containing organic treatment in this invention is treating the catalyst with ammonia gas or gaseous nitrogen-containing organic, the gas can be diluted with inert gas to achieve a volume concentration ratio less than 100%, namely the volume concentration ratio of the gaseous compound is 1-100%. The dilution with inert gas facilitates to accurately control the adding amount of carbon and/or nitrogen during the treatment. The inert gas involved in this invention comprises but not limited to nitrogen, helium, argon, hydrogen and so on which are inert for the catalyst or dehydrogenation of alkane. The invention specifically implements $NH_3$ gas, nitrogen diluted $NH_3$, nitrogen diluted nitrogen-containing organic gas, the treating temperature is in the range of 10-700° C., preferably 300-600° C., the treating time is 1-400 min, preferably 5-150 min.

It is important for most alkane dehydrogenation catalyst that the coke deposition on the catalyst surface should be avoided as far as possible in order to avoid the catalyst deactivation. However, this invention unexpectedly found that the treatment using nitrogen-containing organic makes the surface of the catalyst covered by CN layer, which unexpectedly improves the conversion and selectivity. In addition, the inventors found that the conversion and selectivity of the catalyst can also be improved by the treatment only using $NH_3$.

Further, the present invention protects a regeneration method I of metal supported catalyst, the metal supported catalyst is a $M_a$-$M_b$-$M_c$ metal supported catalyst, wherein the content of $M_c$ is 0 wt %, comprises:

step A, removing the substances which cause the metal supported catalyst poisoned or deactivated to regenerate the metal supported catalyst;

step B, treating the catalyst obtained from step A with ammonia or nitrogen-containing organic at 10-700° C. to obtain the activated catalyst.

In the step A, the substances which cause the catalyst deactivated can be removed by conventional methods, the substances comprise coke, sulfur and so on. The removing method comprises: oxidation removing by O or air, or removing by the reaction between the substances with $H_2$, $CO_2$ or water vapor. This invention carries out oxidation removing by air.

$M_a$ is active metal which is selected from one or more combinations of noble metal and transition metal, wherein the noble metal is selected from one or more mixtures of Pt, Au, Ru, Rh, Pd, Ir and Ag, the transition metal is selected from La, Fe, Co, Mn, Cr, Ni and Cu; preferably the active metal is Pt, Ru, Pd, Ir, Cr, Ni, PtPd, IrPt, IrPd, or IrPtPd. $M_b$ metal is selected from one or more combinations of Zn, Co and Al, preferably Zn, Co or Zn—Co mixed metal.

The support is common catalyst support in this field, and any catalyst support which plays a role of loading can be used. Further, the support is selected from alumina, silica-alumina, zirconia, cerium oxide, titanium oxide, molecular sieves and the mixture containing any two or more of them. This invention carries out γ-alumina, titanium oxide, silica and NaY molecular sieve.

The $M_a$ metal is loaded on the support in a state of single-atom sites, or in a state of coexistence of single-atom sites with clusters and/or nanoparticles; specifically comprising: in the state of single-atom sites, in the state of coexistence of single-atom sites and clusters, or in the state of coexistence of single-atom sites, clusters and nanoparticles; the content of $M_a$ is 0.01-5 wt %, preferably 0.05-2 wt % based on catalyst weight; the content of $M_b$ is 0.1-20 wt %, preferably 0.1-10 wt %, especially preferably 0.5-4 wt % based on catalyst weight;

In the step B, the ammonia comprises ammonia gas or substance that can release ammonia, wherein substance that can release ammonia comprises urea, ammonium nitrate, hexamethylenetetramine or ammonium nitrate, optionally, the substance and the catalyst are placed in the same room, the substance releases $NH_3$ by heating or adding alkali, and the $NH_3$ interacts with catalyst.

The nitrogen-containing organic is selected from $C_{1-6}$ alkyl amine, $C_{2-6}$ alkenyl amine, $C_{6-20}$ aryl amine, $C_{4-20}$ cyclic alkyl amine, $C_{4-20}$ nitrogen-containing heterocyclic ring, $C_{4-20}$ nitrogen-containing heteroaromatic ring and $(RCO)_xNR_{3-x}$, wherein R is H or $C_{1-6}$ alkyl, x is 1 or 2; the amine is a monamine or polyamine; preferably, the alkyl, alkenyl, aryl, nitrogen-containing heterocycle ring, nitrogen-containing heteroaromatic ring are independently further substituted by oxygen, carbonyl, carboxyl, ester group, or amino group; the aromatic is monocyclic aryl or fused polycyclic aryl; the nitrogen-containing heterocyclic ring is monocyclic or fused non-aromatic ring containing cyclic nitrogen atom, and a cyclic carbon atom is optionally replaced by oxygen the nitrogen-containing heteroaromatic ring is monocyclic or fused polycyclic heteroaromatic ring containing cyclic nitrogen atom, and a cyclic carbon is optionally replaced by oxygen. The nitrogen-containing organic is preferably $C_{1-6}$ alkyl amine, $C_{1-6}$ alkyl diamine, $C_{6-20}$ aryl amine, or dimethyl formamide. The nitrogen-containing organic specifically carried out in this invention is ethylenediamine, triethylamine, butylamine, aniline or dimethyl formamide; preferably ethylenediamine.

In the step B, the treatment with ammonia or nitrogen-containing organic is treating the catalyst with ammonia gas or gaseous nitrogen-containing organic, the gas can be diluted with inert gas to achieve a volume concentration ratio less than 100%, namely the volume concentration of the gaseous compound is 1-100% The use of inert gas dilution facilitates to accurately control the adding amount of carbon and/or nitrogen during the treatment. The inert gas in this invention comprises but not limited to nitrogen, helium, argon, hydrogen and so on which is inert for the catalyst or dehydrogenation of alkane. The invention specifically implements $NH_3$ gas, nitrogen diluted $NH_3$, nitrogen diluted nitrogen-containing organic gas, the treating temperature is in the range of 10-700° C., preferably 300-600° C., the treating time is 1-400 min, preferably 5-150 min.

This invention further provides a treatment method II for $M_a$-$M_b$-$M_c$ metal supported catalyst, the method comprises treating the $M_a$-$M_b$-$M_c$ metal supported catalyst precursor with ammonia or nitrogen-containing organic in the range of room temperature to 700° C., wherein $M_a$ is Ir, the first promoter $M_b$ is selected from Zn, Sn and the mixture thereof, the second promoter $M_c$ is selected from K, Na and the mixture thereof, the content of $M_a$ is 0.1-2 wt % based on catalyst weight, the content of first promoter $M_b$ is 0.1-3.0 wt % based on catalyst weight, the content of second promoter $M_c$ is 0.1-2.0 wt % based on catalyst weight, the support is alumina, preferably shaped alumina support, the $M_a$ metal is loaded on the support in a state of single-atom sites, clusters or nanoparticles; preferably in the state of single-atom sites, or in the state of coexistence of single-atom sites with clusters and/or nanoparticles;

wherein the ammonia comprises ammonia gas or substance that can release ammonia; the nitrogen-containing organic is selected from $C_{1-6}$ alkyl amines, $C_{2-6}$ alkenyl amine, $C_{6-20}$ aryl amine, $C_{4-20}$ cyclic alkyl amine, $C_{4-20}$ nitrogen-containing heterocyclic ring, $C_{4-20}$ nitrogen-containing heteroaromatic ring and $(RCO)_xNR_{3-x}$, wherein R is H or $C_{1-6}$ alkyl, x is 1 or 2; the amine is a monamine or polyamine; preferably, the alkyl, alkenyl, aryl, nitrogen-containing heterocycle ring, nitrogen-containing heteroaromatic ring are independently further substituted by oxygen, carbonyl, carboxyl, ester group, or amino group; the aryl is monocyclic aryl or fused polycyclic aryl; the nitrogen-containing heterocyclic ring is a monocyclic or fused non-aromatic ring containing cyclic nitrogen atom, and a cyclic carbon atom is optionally replaced by oxygen; the nitrogen-containing heteroaromatic ring is a monocyclic or fused polycyclic heteroaromatic ring containing cyclic nitrogen atom, and a cyclic carbon atom is optionally replaced by oxygen.

In the treatment method II, preferably, the preparation method of the catalyst precursor is loading the $M_a$ metal precursor, $M_b$ precursor and $M_c$ precursor on the support to form the catalyst precursor, the $M_a$ metal precursor is soluble inorganic salt, organic salt or metal complex of $M_a$ metal in a solvent, preferably nitrate, chloride, sulphate, acetate, acetylacetone salt or complex, the $M_b$ or $M_c$ metal precursor is soluble organic or inorganic salt of $M_b$ or $M_c$ in a solvent, preferably nitrate, chloride, sulphate, acetate, oxalate or acetylacetone salt; the solvent is water or alcohol, wherein the alcohol is methanol or ethanol.

In the treatment method II, preferably, the preparation process of the catalyst precursor comprises, optionally, aging at the range of room temperature to 80° C., the aging time is 0.5-40 h, preferably 2-8 h; optionally, after aging, drying at 60-150° C., preferably 80-120° C., the drying time is 2-20 h, preferably 6-10 h; calcining the dried catalyst at 400-600° C., the calcining time is 3-6 h, to obtain the catalyst precursor.

In the treatment method II, preferably, the ammonia is ammonia gas, the nitrogen-containing organic is preferably ethylenediamine, triethylamine, butylamine, aniline or dimethyl formamide.

Preferably, in the treatment method II, treating with gaseous ethylenediamine at 300-600° C., the gaseous ethylenediamine is optionally the mixture of ethylenediamine and nitrogen in a volume ratio of 1-5:20-24, the treating time is 0.05-4 h, preferably 0.5-1.5 h.

In the treatment method II, preferably, the catalyst is Ir/Zn/K@$Al_2O_3$, Ir/Sn/K@$Al_2O_3$, Ir/Zn/Na@$Al_2O_3$, Ir/Sn/Na@$Al_2O_3$, wherein the content of Ir is 0.1-2 wt % based on catalyst weight, the content of Zn or Sn is 01-3.0 wt % based on catalyst weight, and the content of K or Na is 0.1-2.0 wt % based on catalyst weight.

This invention also provides a regeneration method II for $M_a$-$M_b$-$M_c$ supported catalyst, comprises:
  step A, removing the substances which cause the $M_a$-$M_b$-$M_c$ metal supported catalyst poisoned or deactivated to regenerate the catalyst;
  step B, treating the catalyst with ammonia or nitrogen-containing organic in the range of room temperature to 700° C. to obtain the activated catalyst.
  wherein $M_A$ is Ir, the first promoter $M_b$ is selected from Zn, Sn and the mixture of both, the second promoter $M_c$ is selected from K, Na or the mixture of them, the content of $M_a$ is 0.1-2 wt % based on catalyst weight, the content of the first promoter $M_b$ is 0.1-3.0 wt % based on catalyst weight, the content of the second promoter $M_c$ is 0.1-2.0 wt % based on catalyst weight, the support is alumina, preferably shaped alumina support; The $M_a$ metal is dispersed and loaded on the support in a state of single-atom sites, clusters or nanoparticles; preferably in the state of single-atom sites, or in the state of coexistence of single-atom sites with clusters and/or nanoparticles;
  In the step A, the substances which cause the catalyst poisoned or deactivated comprise coke and/or sulfur, the removing process comprises: oxidation removing by $O_2$ or air, or reduction removing by $H_2$;
  In the step B, the catalyst is treated with ammonia or nitrogen-containing organic, wherein the nitrogen-containing organic is preferably selected from ethylenediamine, triethylamine, butylamine, aniline and dimethyl formamide, the treatment temperature is further preferably 300-700° C.

In the regeneration method II, preferably, in the step B, treating with gaseous ethylenediamine in the range of 400-600° C., preferably treating with the mixture of ethylenediamine and nitrogen in a volume ratio of 1-5:20-24.

This invention further provides use of catalyst in preparing $C_{2-6}$ olefin by dehydrogenation of $C_{2-6}$ alkane, the catalyst is obtained by the treatment method mentioned above, activation method mentioned above and regeneration method mentioned above.

This invention also provides a method for preparing light olefin by the dehydrogenation of corresponding light alkane, comprise: using a catalyst obtained by the treatment method mentioned above, activation method mentioned above or regeneration method mentioned above, Preferably, to catalyze dehydrogenation of $C_{2-6}$ alkane to obtain corresponding $C_{2-6}$ olefin.

Another aspect of the present invention is to protect a method for the dehydrogenation of light alkane to prepare corresponding light olefin, comprise: catalyzing the dehydrogenation of light alkane to obtain corresponding light olefin by the catalyst after CN (carbon-nitrogen) treatment. The light alkane is $C_{2-6}$ alkane, including ethane, propane, butane, isobutane, or the mixture of two or more light alkanes, the dehydrogenation of propane to propylene has been carried out in this invention.

The Terms Used Herein are Defined as Follows

The single-atom sites state, single-atom state, single-atom distribution, single-atom form or single-atom level dispersed state involved in this invention means that active metal element is in an isolated state that the metallic atoms (ions) are independently separated from each other so that there is no metal-metal bond between the active metal atoms and the atoms exist in an atom level dispersion or in a single-atom sites state. The metal dispersed in a single-atom sites state may be in an atomic state, or in an ionic state, but most of time in a state between the atomic state and the ionic state. It is well know that the metal atoms in nanoparticles are bonded to each other, which do not belong to the single-atom state or single-atom dispersed state defined by this invention. Although the metal atoms are separated by other elements in the compound or mixture nanoparticles formed by metal and other elements (e g., O, S or even other metals), moreover, the structures are easy to converted into nanoparticles in metal state (such as oxides nanoparticles convert by reduction), the compound or mixture nanoparticles formed by metal and other elements also do not belong to the single-atom sites state or single-atom dispersed state defined by this invention.

In theory, the metal atoms in the single-atom sites state protected by this invention are completely independent from each other. But the random deviation of preparation operation condition in different batches causes the obtained product does not exclude the presence of a bit of metal species in agglomeration state, such as clusters comprising a small amount of atoms or ions. It also does not exclude the presence of a bit of metal nanoparticles. In other words, active metal in the catalyst of the invention may be in a state of single atom sites dispersed, at the same time, a part of it may be in a state of clusters of aggregated metal atoms, and/or a part of it may be in a state of nanoparticles. The single-atom state protected in this application requires a certain proportion of single-atom of noble metal in different forms of existence such as single-atom of noble metal, clusters of noble metal and nanoparticles of noble metal in the catalyst, such as higher than 10%, preferably higher than 20%, especially preferably higher than 50% But limited to the current technical means, the approximate ratio of single-atom state can only be calculated through the relatively rough statistical means, which is randomly selecting a large number of different local area from the catalyst test sample to analyze and characterize by aberration-corrected high-resolution transmission electron microscopy and randomly selecting various forms of noble metal state for statistical analysis, or is analyzing the catalyst sample by extended X-ray absorption fine structure (EXAFS), which can characterize the overall information of samples, to estimate the ratio of metal and other atom bonding signals to metal-metal bonding signals. It should be noted that, as long as the technology of this invention is used in the product to obtain the catalyst product with even only partial single-atom state, the product also exhibits an improved performance. Therefore, as long as a catalyst with alkane dehydrogenation activity prepared according to the method of this invention, it should fall within the protection scope of the present application.

Alkyl amine represents an alkane with one or more amino groups, the said alkane can be substituted by one or more $C_{1-6}$ alkyl groups, $C_{4-20}$ cycloalkyl groups or $C_{6-20}$ aromatic groups, or the C—C bond in the alkane above can be replaced by unsaturated olefin or alkyne to form an unsaturated carbon chain; $C_{6-20}$ aromatic amine mentioned above represents aromatic amino compound with 6-20 carbon atoms, $C_{4-20}$ nitrogen-containing heteroaromatic ring represents the organics possess a characteristic of aromatic 2n+4, and part of cyclic carbon atoms is replaced by heteroatom, in which the heteroatom is O or N atom. $C_{4-20}$ nitrogen-containing heterocyclic ring represents the organics with nitrogen-containing heterocyclic ring containing 4-20 cyclic carbon atoms; $C_{4-20}$ cyclic alkyl amine represents a cycloalkane containing 4-20 cyclic carbon atoms and the cycloalkane contains one or more amino groups. The above cycloalkyl, nitrogen-containing heterocyclic ring and aromatic ring are monocyclic or fused polycyclic ring, the ring can be further substituted by $C_{1-6}$ alkyl.

The content of the metals, including noble metal and transition metal, is measured by metal elements, that is, only the mass percentage of the metals is calculated.

The mentioned substance that can release ammonia is the inorganic substance or organic substance can release $NH_3$, such as urea, ammonia water, hexamethylenetetramine and ammonium nitrate.

The room temperature refers to a temperature without additional heating. Due to changes of room temperature depending on the difference of region, season or indoor environment, however, the room temperature generally refers to a temperature above 10° C.

The activation, also called catalyst pretreatment, are usually carried out after loading the catalyst in the reactor. The catalyst after the activation process exhibits a higher conversion and/or a higher selectivity.

The regeneration, also called catalyst reactivation, usually refers to the process to recover catalytic activity of deactivated catalyst.

Complex is also known as coordination compound, including complex formed by noble metal or transition metal with ligand, common ligand comprises halogen (fluorine, chlorine, bromine, iodine), nitro, nitroso, cyanide, ammonia, water or organic group, common complex comprises chlorine complex, ammonia complex, cyanide complex and so on, including chloroplatinic acid, chloroplatinic acid salt, chloroplatinic acid hydrate. Refer to "Handbook for the Synthesis of Noble Metal Compound and Complex (Precision)" (Yu Jianmin, 2009, Chemical Industry Press).

Beneficial Effects

1. After being treated by this invention method, the supported $M_a$-$M_b$ metallic catalyst has obviously improved conversion and selectivity for direct dehydrogenation of light alkane, realizing the preactivation of the catalyst.
2. The catalyst preparation method of this invention is simple, so that the catalyst can be prepared efficiently and produced in a large scale.
3. The catalyst obtained by the preparation method of this invention is stable, the activity of the catalyst remains

DESCRIPTION OF PICTURES

EXAMPLES

Figure 1:
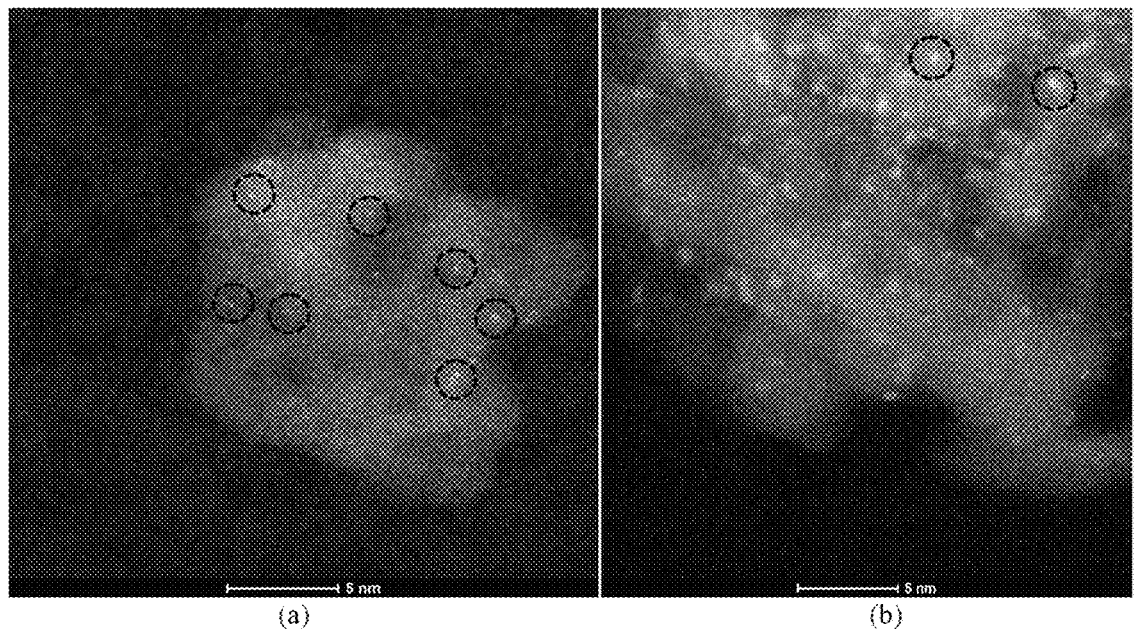
FIG. 1 shows aberration-corrected scanning transmission electron microscopy images of the fresh catalyst, in which (a) shows the metal in the single-atom sites state (part of it is cycled by dashed line); (b) shows the existence of clusters or nanoparticles of metal in the catalyst.

The terms and explanations for the Examples are as follows:
concentration of metal precursor: the concentration is calculated by the mass of the metal element. For example, aqueous solution of Pd with concentration of 0.02 g/g represents the amount of the Pd element is 0.02 g in 1 g of solution
microreactor fixed-bed microreactor or microreactor device.
microreactor tail gas, the tail gas generated after reaction in fixed-bed microreactor or microreaction device.
min: minute.
wt %: mass percent
TEM: transmission electron microscope.
HR-TEM: high-resolution transmission electron microscope.
AC-STEM: aberration-corrected scanning transmission electron microscopy.

The technology of the present invention will be further described below by dehydrogenation of propane.

Preparation Example 1: Preparation of Active Metal/Zinc Supported Catalyst 1.1 $Ir_{(0.1\ wt\ \%)}Zn_{(3\ wt\ \%)}/Al_2O_3$ 0.5 g of $IrCl_3 \cdot 3H_2O$ and 0.5 g of NaCl were weighed, completely dissolved in 19 g of water at 80° C. 16.4 g of $Zn(NO_3)_2 \cdot 6H_2O$ was dissolved in 7.4 g of the solution above. After dissolving, the volume of the solution was diluted to the saturation impregnation volume of small spheres. The above solution was impregnated in 96.9 g of alumina spheres with equal volume, and dried at 120° C. overnight. Ir/Zn catalyst (Or 0.1 wt %; Zn 3 wt %) was obtained, which was marked as $Ir_{(0.1\ wt\ \%)}Zn_{(3\ wt\ \%)}/Al_2O_3$.

$Ir_{(0.3\ wt\ \%)}Zn_{(3\ wt\ \%)}/Al_2O_3$ 8.25 g of $Zn(NO)_2 \cdot 6H_2O$ was dissolved in water, the volume of the solution was diluted to the saturation impregnation volume of alumina spheres. The solution above was impregnated in 50 g of alumina spheres with equal volume, aged at room temperature for 6 h and further dried overnight at 120° C., and then calcined at 600° C. for 4 h to obtain a sample. 0.5 g of $IrCl_3 \cdot 3H_2O$ and 0.5 g of NaCl were weighed, completely dissolved in 19 g of water at 80° C. The volume of 2.2 g of the solution above was further diluted to the saturation impregnation volume of the sample 10 g of the sample was impregnated in the solution above with equal volume, dried overnight at 120° C., then calcined at 400° C. for 1 h, to obtain Ir/Zn catalyst (Ir 0.3 wt %; Zn 3 wt %) which was marked as $Ir_{(0.3\ wt\ \%)}Zn_{(3\ wt\ \%)}/Al_2O_3$.

1.2 $Pt_{(0.3\ wt\ \%)}Zn_{(1\ wt\ \%)}/Al_2O_3$

Chloroplatinic acid (containing 0.015 g of Pt) and zinc nitrate (containing 0.05 g of Zn) were weighed and dissolved in water, and the volume of the solution was diluted to 2.21 mL of saturation impregnation volume of alumina spheres. Sg of alumina spheres were weighed and the solution above was impregnated in the alumina spheres, dried for 8 h at 80° C., calcined at 600° C. for 4 h, to obtain Pt/Zn catalyst (Pt 0.3 wt %, Zn 1 wt %), which was marked as $Pt_{(0.3\ wt\ \%)}Zn_{(1\ wt\ \%)}/Al_2O_3$.

1.3 $Cr-Zn/Al_2O_3$ (200713a)

Preparation of 100 g of Cr and Zn supported alumina catalyst with loading amount of 0.5 wt % of Cr and 1.5 wt % of Zn: 3.85 g of chromium nitrate nonahydrate and 6.82 g of zinc nitrate hexahydrate were taken and dissolved in ethanol, diluted to 83.3 g, then 98 g of alumina was added, and a rotary evaporation was carried out at 40° C. After ethanol was completely evaporated and chromium and zinc species were fully loaded on the surface of alumina, the Cr—Zn supported $Al_2O_3$ catalyst was obtained, which was marked as $Cr_{(0.5\ wt\ \%)}Zn_{(1.5\ wt\ \%)}/Al_2O_3$.

1.4 $Mn-Zn/Al_2O_3$ (d200829a)

Preparation of 100 g of Mn and Zn supported alumina catalyst with loading amount of 0.5 wt % of Mn and 1.5 wt % of Zn: 1.80 g of manganese nitrate tetrahydrate and 6.82 g of zinc nitrate hexahydrate were taken and dissolved in ethanol, diluted to 919 g. then 98 g of alumina was added, and a rotary evaporation was carried out at 40° C. After ethanol was completely evaporated and manganese and zinc species were fully loaded on the surface of alumina, the Mn—Zn supported $Al_2O_3$ catalyst was obtained, which was marked as $Mn_{(0.5\ wt\ \%)}Zn_{(1.5\ wt\ \%)}/Al_2O_3$.

1.5 $Fe-Zn/Al_2O_3$ (200713b)

Preparation of 100 g of Fe and Zn supported alumina catalyst with loading amount of 0.5 wt % of Fe and 1.5 wt % of Zn: 3.62 g of ferric nitrate nonahydrate and 6.82 g of zinc nitrate hexahydrate were taken and dissolved in ethanol, diluted to 83.3 g, then 98 g of alumina was added, and a rotary evaporation was carried out at 40° C. After ethanol was completely evaporated and iron and zinc species were fully loaded on the surface of alumina, the Fe—Zn supported $Al_2O_3$ catalyst was obtained, which was marked as $Fe_{(0.5\ wt\ \%)}Zn_{(1.5\ wt\ \%)}/Al_2O_3$.

1.6 $Co-Zn/Al_2O_3$ (200918a)

Preparation of 100 g of Co and Zn supported alumina catalyst with loading amount of 0.5 wt % of Co and 1.5 wt % of Zn: 2.47 g of cobalt nitrate hexahydrate and 6.82 g of zinc nitrate hexahydrate were taken and dissolved in ethanol, diluted to 83.3 g, then 98 g of alumina was added, and a rotary evaporation was carried out at 40° C. After ethanol was completely evaporated and cobalt and zinc species were fully loaded on the surface of alumina, the Co—Zn supported $Al_2O_3$ catalyst was obtained, which was marked as $Co_{(0.5\ wt\ \%)}Zn_{(1.5\ wt\ \%)}/Al_2O_3$.

1.7 $Ni-Zn/Al_2O_3$ (200918b)

Preparation of 100 g of Ni and Zn supported alumina catalyst with loading amount of 0.5 wt % of Ni and 1.5 wt % of Zn: 2.48 g of nickel nitrate hexahydrate and 6.82 g of zinc nitrate hexahydrate were taken and dissolved in ethanol, diluted to 83.3 g, then 98 g of alumina was added, and a rotary evaporation was carried out at 40° C. After ethanol was completely evaporated and nickel and zinc species were fully loaded on the surface of alumina, the Ni—Zn supported $Al_2O_3$ catalyst was obtained, which was marked as $Ni_{(0.5\ wt\ \%)}Zn_{(105\ wt\ \%)}/Al_2O_3$.

1.8 Cu—Zn/Al$_2$O$_3$ (d200730)

Preparation of 100 g of Cu and Zn supported alumina catalyst with loading amount of 0.5 wt % of Cu and 1.5 wt % of Zn: 1.90 g of copper nitrate trihydrate and 6.82 g of zinc nitrate hexahydrate were taken and dissolved in ethanol, diluted to 92.0 g, then 98 g of alumina was added, and a rotary evaporation was carried out at 40° C. After ethanol was completely evaporated and copper and zinc species were fully loaded on the surface of alumina, the Cu—Zn supported Al$_2$O$_3$ catalyst was obtained, which was marked as Cu$_{(0.5\ wt\ \%)}$Zn$_{(1.5\ wt\ \%)}$/Al$_2$O$_3$.

1.9 La—Zn/Al$_2$O$_3$ (d200829b)

Preparation of 100 g of La and Zn supported alumina catalyst with loading amount of 0.5 wt % of La and 1.5 wt % of Zn: 1.34 g of lanthanum nitrate heptahydrate and 6.82 g of zinc nitrate hexahydrate were taken and dissolved in ethanol, diluted to 914 g, then 98 g of alumina was added, and a rotary evaporation was carried out at 40° C. After ethanol was completely evaporated and lanthanum and zinc species were fully loaded on the surface of alumina, the La—Zn supported Al$_2$O$_3$ catalyst was obtained, which was marked as La$_{(0.5\ wt\ \%)}$Zn$_{(1.5\ wt\ \%)}$Al$_2$O$_3$.

1.10 Ir$_{(0.1\ wt\ \%)}$Co$_{(0.5\ wt\ \%)}$Zn$_{(1\ wt\ \%)}$/Al$_2$O$_3$ (200608b)

0.37 g of IrCl$_3$·3H$_2$O and 0.36 g of NaCl were dissolved in water under heating condition and further diluted to 40.0 g with water in advance to obtain an aqueous solution with an Ir concentration of 0.005 g/g. 1.0 g of the aqueous solution was taken, then 0.11 g of cobalt nitrate hexahydrate and 0.23 g of zinc nitrate hexahydrate were added into the solution. The mixture was dissolved in ultrapure water and diluted to 2.2 g, then 4.9 g of alumina spheres was added for equal volume impregnation, then dried overnight at 120° C., the Ir—Co—Zn supported Al$_2$O$_3$ catalyst was obtained, which was marked as Ir$_{(0.1\ wt\ \%)}$Co$_{(0.5\ wt\ \%)}$Zn$_{(1\ wt\ \%)}$/Al$_2$O$_3$.

1.11 Ir$_{(0.1\ wt\ \%)}$Co$_{(0.75\ wt\ \%)}$Zn$_{(0.75\ wt\ \%)}$/Al$_2$O$_3$ (200608c)

0.37 g of IrCl$_3$·3H$_2$O and 0.36 g of NaCl were dissolved in water under heating condition and further diluted to 40.0 g with water in advance to obtain an aqueous solution with an Ir concentration of 0.005 g/g. 1.0 g of the aqueous solution was taken, then 0.17 g of cobalt nitrate hexahydrate and 0.17 g of zinc nitrate hexahydrate were added into the solution. The mixture was dissolved in ultrapure water and further diluted to 2.2 g, then 4.9 g of alumina spheres was added for equal volume impregnation, then dried overnight at 120° C., the Ir—Co—Zn supported Al$_2$O$_3$ catalyst was obtained, which was marked as Ir$_{(0.1\ wt\ \%)}$Co$_{(0.75\ wt\ \%)}$Zn$_{(0.75\ wt\ \%)}$/Al$_2$O$_3$.

1.12 Ir$_{(0.1\ wt\ \%)}$Co$_{(1.5\ wt\ \%)}$/Al$_2$O$_3$ (200611 d)

0.37 g of IrCl$_3$·3H$_2$O and 0.36 g of NaCl were dissolved in water under heating condition and further diluted to 40.0 g with water in advance to obtain an aqueous solution with an Ir concentration of 0.005 g/g. 1.0 g of the aqueous solution was taken, then 0.33 g of cobalt nitrate hexahydrate was added into the solution. The mixture was dissolved in ultrapure water and further diluted to 2.2 g, then 4.9 g of alumina spheres was added for equal volume impregnation, then dried overnight at 120° C., the Ir—Co supported Al$_2$O$_3$ catalyst was obtained, which was marked as Ir$_{(0.1\ wt\ \%)}$Co$_{(1.5\ wt\ \%)}$/Al$_2$O$_3$.

1.13 The catalyst was prepared, which was marked as Ir$_{(0.1\ wt\ \%)}$Zn$_{(1.5\ wt\ \%)}$Al$_{(1.24\ wt\ \%)}$/Al$_2$O$_3$ 1.14 The catalyst was prepared, which was marked as Ir$_{(0.15\ wt\ \%)}$Zn$_{(1.5\ wt\ \%)}$Al$_{(1.24\ wt\ \%)}$/Al$_2$O$_3$ 1.15 Ir$_{(0.1\ wt\ \%)}$Zn$_{(1\ wt\ \%)}$/NaY molecular sieve 5 g of NaY molecular sieve pellets were weighed, then over-volume impregnated in an aqueous solution containing 0.26% of IrCl$_3$ and 7.8% of Zn(NO$_3$)$_2$ for 30 min. After solid-liquid separation, the solid was dried overnight at 120° C. to obtain the Ir/Zn catalyst (Ir 0.15 wt %; Zn 1.5 wt %).

1.16 Ir$_{(0.3\ wt\ \%)}$Zn$_{(3\ wt\ \%)}$/SiO$_2$ 0.5 g of IrCl$_3$·3H$_2$O and 0.5 g of NaCl were weighed and completely dissolved in 19 g of water at 80° C. 0.8 g of Zn(NO$_3$)$_2$·6H$_2$O was dissolved in 1.1 g of the solution above, then the volume of the obtained solution was diluted to the saturation impregnation volume of silica pellets. The above solution was impregnated in 5 g of silica pellets with equal volume, and further dried overnight at 120° C., to obtain Ir/Zn catalyst (Ir 0.3 wt %; Zn 3 wt %).

Preparation Example 2: Pretreatment Method for the Regeneration of Catalyst

Catalyst was regenerated in this experiment, the catalyst to be treated was calcined at 400-450° C. for 3 h in air atmosphere with a flow of 49.8 mL/min to remove coke, and a regenerated catalyst was obtained.

Application Test Example 3: Experimental Method for Dehydrogenation of Alkane

This invention takes the dehydrogenation of propane to prepare propylene as an example.

The catalytic performance of catalyst was evaluated with continuous flow fixed bed reactor, in which 1.0 g of catalyst was loaded in a straight quartz reaction tube with an inner diameter of 10 mm.

The catalyst was treated or activated.

The reaction temperature of 600° C. was controlled by a tubular resistance furnace. The flow rate of reaction gas was controlled by mass flow meter. Before and after reaction, the reaction tube was purged with nitrogen or other inert gas.

The reaction product was analyzed by Shimadzu gas chromatograph equipped with an HP-PLOT Al$_2$O$_3$S capillary column.

Example 1

1 g of the Ir/Zn catalyst (Ir 0.1 wt %, Zn 3 wt %) prepared by Preparation Example 1.1 was weighed, treated at 500° C. under 100% ammonia gas atmosphere for 30 min. Pure propane gas (volume space velocity: 1000 h$^{-1}$) was introduced for reaction at 600° C., and the conversion and selectivity of direct catalytic dehydrogenation reaction of propane were tested.

Examples 2 to 11

Referring to the experimental operations in Example 1, N$_2$ was used as diluent gas to adjust the concentration of ammonia, treatment temperature, treatment time were adjusted, the other operations were the same as those in Example 1. The specific adjustments are shown as follow:

In Example 2, the ammonia concentration was 80% (N$_2$ 2.6 mL/min, NH$_3$ 10.5 mL/min), treatment temperature was 500° C., and treatment time was 30 min.

In Example 3, the ammonia concentration was 50% (N$_2$ 6.55 mL/min, NH$_3$ 6.55 mL/min), treatment temperature was 500° C., and treatment time was 30 min.

In Example 4, the ammonia concentration was 20% (N$_2$ 10.5 mL/min, NH$_3$ 2.6 mL/min), treatment temperature was 500° C., and treatment time was 30 min.

In Example 5, the ammonia concentration was 3% (N$_2$ 12.7 mL/min, NH$_3$ 0.4 mL/min), treatment temperature was 500° C., and treatment time was 30 min.

In Example 6, the ammonia concentration was 3% ($N_2$ 12.7 mL/min, $NH_3$ 0.4 mL/min), treatment temperature was 500° C. and treatment time was 15 min.

In Example 7, the ammonia concentration was 3% ($N_2$ 12.7 mL/min, $NH_3$ 0.4 mL/min), treatment temperature was 500° C., and treatment time was 30 min.

In Example 8, the ammonia concentration was 3% ($N_2$ 12.7 mL/min, $NH_3$ 0.4 mL/min), treatment temperature was 500° C., and treatment time was 45 min.

In Example 9, the ammonia concentration was 3% ($N_2$ 12.7 mL/min, $NH_3$ 0.4 mL/min), treatment temperature was 500° C., and treatment time was 75 min.

In Example 10, the ammonia concentration was 3% ($N_2$ 12.7 mL/min, $NH_3$ 0.4 mL/min), treatment temperature was 500° C., and treatment time was 120 min.

In Example 11, the ammonia concentration was 3% ($N_2$ 12.7 mL/min, $NH_3$ 0.4 mL/min), treatment temperature was 500° C., and treatment time was 150 min.

Example 12

1 g of the Ir/Zn catalyst (Ir 0.1 wt %; Zn 3 wt %) prepared by Preparation Example 1.1 was weighed, treated at 500° C. under 2% ethylenediamine/nitrogen atmosphere for 15 min. Pure propane gas (volume space velocity: 1000 $h^{-1}$) was introduced for reaction at 600° C., and the conversion and selectivity of direct catalytic dehydrogenation of propane were evaluated.

Example 13

1 g of the Ir/Zn catalyst (Ir 0.1 wt %; Zn 3 wt %) prepared by Preparation Example 1.1 was weighed, treated at 500° C. under 2% ethylenediamine/nitrogen atmosphere for 60 min. Pure propane gas (volume space velocity: 1000 $h^{-1}$) was introduced for reaction at 600° C., and the conversion and selectivity of direct catalytic dehydrogenation of propane were evaluated.

Example 14

1 g of the Ir/Zn catalyst (Ir 0.1 wt %; Zn 3 wt %) prepared by Preparation Example 1.1 was weighed, treated at room temperature (10° C.) under 4% ethylenediamine/nitrogen atmosphere for 30 min Pure propane gas (volume space velocity. 1000 $h^{-1}$) was introduced for reaction at 600° C., and the conversion and selectivity of direct catalytic dehydrogenation reaction of propane were tested.

Example 15

1 g of the Ir/Zn catalyst (Ir 0.1 wt %; Zn 3 wt %) prepared by Preparation Example 1.1 was weighed, treated at 700° C. under 4% ethylenediamine/nitrogen atmosphere for 30 min. Pure propane gas (volume space velocity: 1000 h−1) was introduced for reaction at 600° C. and the conversion and selectivity of direct catalytic dehydrogenation reaction of propane were tested.

Example 16

1 g of the Ir/Zn catalyst (Ir 0.1 wt %; Zn 3 wt %) prepared by Preparation Example 1.1 was weighed, treated at 500° C. under 1% ethylenediamine/nitrogen atmosphere for 30 min. Pure propane gas (volume space velocity: 1000 $h^{-1}$) was introduced for reaction at 600° C., and the conversion and selectivity of direct catalytic dehydrogenation reaction of propane were tested.

Example 17

1 g of the Ir/Zn catalyst (Ir 0.1 wt %; Zn 3 wt %) prepared by Preparation Example 1.1 was weighed, treated at 500° C. under 4% n-butylamine/nitrogen atmosphere for 30 min. Pure propane gas (volume space velocity: 1000 $h^{-1}$) was introduced for reaction at 600° C., and the conversion and selectivity of direct catalytic dehydrogenation reaction of propane were tested.

Example 18

1 g of the Ir/Zn catalyst (Ir 0.1 wt %; Zn 3 wt %) prepared by Preparation Example 1.1 was weighed, treated at 500° C. under 4% triethylamine/nitrogen atmosphere for 30 min. Pure propane gas (volume space velocity: 1000 $h^{-1}$) was introduced for reaction at 600° C., and the conversion and selectivity of direct catalytic dehydrogenation reaction of propane were tested.

Example 19

1 g of the Ir/Zn catalyst (Ir 0.1 wt %; Zn 3 wt %) prepared by Preparation Example 1.1 was weighed, treated at 500° C. under 4% aniline/nitrogen atmosphere for 30 min. Pure propane gas (volume space velocity: 1000 $h^{-1}$) was introduced for reaction at 600° C., and the conversion and selectivity of direct catalytic dehydrogenation reaction of propane were tested.

Example 20

1 g of the Ir/Zn catalyst (Ir 0.1 wt %; Zn 3 wt %) prepared by Preparation Example 1.1 was weighed, treated at 500° C. under 4% DMF/nitrogen atmosphere for 30 min. Pure propane gas (volume space velocity: 1000 $h^{-1}$) was introduced for reaction at 600° C. and the conversion and selectivity of direct catalytic dehydrogenation reaction of propane were tested.

Example 21

1 g of the Pt/Zn catalyst (Pt 0.3 wt %; Zn 1 wt %) prepared by Preparation Example 1.2 was weighed, treated at 500° C. under 4% ethylenediamine/nitrogen atmosphere for 30 min. Pure propane gas (volume space velocity: 1000 $h^{-1}$) was introduced for reaction at 600° C., and the conversion and selectivity of direct catalytic dehydrogenation reaction of propane were tested.

Examples 22 to 35

Referring to a method similar to Example 1, the 1.3-1.16 metal supported catalysts prepared by Preparation Example 1 were weighed respectively, treated at 500° C. under 4% ethylenediamine/nitrogen atmosphere for 30 min respectively. Pure propane gas (volume space velocity: 1000 $h^{-1}$) was introduced for reaction at 600° C., and the conversion and selectivity of direct catalytic dehydrogenation reaction of propane were tested.

Example 36 Regeneration Example 1 g of the Ir/Zn catalyst (Ir 0.1 wt %; Zn 3 wt %) prepared by Preparation Example 1.1 was weighed, treated at 500° C.

under 4% ethylenediamine/nitrogen atmosphere for 30 min. At 600° C. and under the condition of 0.25 of hydrogen to hydrocarbon ratio (hydrogen to propane ratio), propane was directly catalyzed for dehydrogenation reaction (propane volume space velocity: 1000 $h^{-1}$), the measured conversion of propane was 40% and the selectivity for propylene was 92% After continuous testing for 6 h, the conversion of propane dropped to 33% and the selectivity for propylene was 93%.

The catalyst after the test above was calcined at 400° C. for 3 h under air atmosphere to remove coke, and the obtained regenerated sample was treated at 500° C. under 4% ethylenediamine/nitrogen atmosphere for 30 min.

At 600° C. and under the condition of 0.25 of hydrogen to propane ratio, propane was directly catalyzed for dehydrogenation reaction (propane volume space velocity: 1000 $h^{-1}$), the measured conversion of propane was 39% and the selectivity for propylene was 93%.

Comparative Example 1

1 g of Ir/Zn catalyst (Ir 0.1 wt %; Zn 3 wt %, alumina support) was weighed and not subjected to any treatment Pure propane gas was introduced for reaction at 600° C. and the conversion and selectivity of direct catalytic dehydrogenation reaction of propane were tested (volume space velocity: 1000 $h^{-1}$).

APPLICATION TEST AND RESULTS

TABLE 1

The treatment conditions and performance comparison of Examples 1 to 20 and Comparative Example 1.

| Example | Catalyst composition | Treatment conditions | | | Optimal performance | |
|---|---|---|---|---|---|---|
| | | Atmosphere and Concentration | Time(min) | Temperature (° C.) | Conversion (%) | Selectivity (%) |
| EX1 | $Ir_{(0.1 wt \%)}Zn_{(3 wt \%)}$/$Al_2O_3$ | 100% ammonia gas | 30 | 500 | 30.1 | 89.07 |
| EX 2 | $Ir_{(0.1 wt \%)}Zn_{(3 wt \%)}$/$Al_2O_3$ | 80% ammonia gas | 30 | 500 | 31.85 | 89.638 |
| EX3 | $Ir_{(0.1 wt \%)}Zn_{(3 wt \%)}$/$Al_2O_3$ | 50% ammonia gas | 30 | 500 | 30 | 89 |
| EX4 | $Ir_{(0.1 wt \%)}Zn_{(3 wt \%)}$/$Al_2O_3$ | 20% ammonia gas | 30 | 500 | 32.41 | 89.88 |
| EX5 | $Ir_{(0.1 wt \%)}Zn_{(3 wt \%)}$/$Al_2O_3$ | 3% ammonia gas | 30 | 500 | 32.83 | 89.55 |
| EX6 | $Ir_{(0.1 wt \%)}Zn_{(3 wt \%)}$/$Al_2O_3$ | 3% ammonia gas | 15 | 500 | 32.45 | 89.33 |
| EX7 | $Ir_{(0.1 wt \%)}Zn_{(3 wt \%)}$/$Al_2O_3$ | 3% ammonia gas | 30 | 500 | 32.83 | 89.55 |
| EX8 | $Ir_{(0.1 wt \%)}Zn_{(3 wt \%)}$/$Al_2O_3$ | 3% ammonia gas | 45 | 500 | 33.65 | 89.78 |
| EX9 | $Ir_{(0.1 wt \%)}Zn_{(3 wt \%)}$/$Al_2O_3$ | 3% ammonia gas | 75 | 500 | 33 | 89.36 |
| EX10 | $Ir_{(0.1 wt \%)}Zn_{(3 wt \%)}$/$Al_2O_3$ | 3% ammonia gas | 120 | 500 | 31.95 | 89.45 |
| EX11 | $Ir_{(0.1 wt \%)}Zn_{(3 wt \%)}$/$Al_2O_3$ | 3% ammonia gas | 150 | 500 | 32.71 | 89.67 |
| EX12 | $Ir_{(0.1 wt \%)}Zn_{(3 wt \%)}$/$Al_2O_3$ | 2% ethylenediamine | 15 | 500 | 30.1 | 89.07 |
| EX13 | $Ir_{(0.1 wt \%)}Zn_{(3 wt \%)}$/$Al_2O_3$ | 2% ethylenediamine | 60 | 500 | 31.85 | 89.638 |
| EX14 | $Ir_{(0.1 wt \%)}Zn_{(3 wt \%)}$/$Al_2O_3$ | 4% ethylenediamine | 30 | 10 | 30 | 89 |
| EX15 | $Ir_{(0.1 wt \%)}Zn_{(3 wt \%)}$/$Al_2O_3$ | 4% ethylenediamine | 30 | 700 | 32.41 | 89.88 |
| EX16 | $Ir_{(0.1 wt \%)}Zn_{(3 wt \%)}$/$Al_2O_3$ | 1% ethylenediamine | 30 | 500 | 32.83 | 89.55 |
| EX17 | $Ir_{(0.1 wt \%)}Zn_{(3 wt \%)}$/$Al_2O_3$ | 4% n-butylamine | 30 | 500 | 32.45 | 89.33 |
| EX18 | $Ir_{(0.1 wt \%)}Zn_{(3 wt \%)}$/$Al_2O_3$ | 4% triethylamine | 30 | 500 | 32.5 | 88.86 |
| EX19 | $Ir_{(0.1 wt \%)}Zn_{(3 wt \%)}$/$Al_2O_3$ | 4% aniline | 30 | 500 | 33.65 | 89.78 |
| EX20 | $Ir_{(0.1 wt \%)}Zn_{(3 wt \%)}$/$Al_2O_3$ | 4% DMF | 30 | 500 | 33 | 89.36 |
| Comparative Example 1 | $Ir_{(0.1 wt \%)}Zn_{(3 wt \%)}$/$Al_2O_3$ | — | — | — | 18 | 84 |

*EX1 represents Example1, and so on.

The test results of Examples 1 to 20 and Comparative Example 1 show that the treatment method of catalyst in the present invention, whether using $NH_3$ or using nitrogen-containing organic, significantly improves the conversion and selectivity of the catalyst, which fully demonstrates the effectiveness of treatment with $NH_3$ and nitrogen-containing organic.

catalyst consists of $Ir_{(0.3\ wt\ \%)}Zn_{(2\ wt\ \%)}/Al_2O_3$, and the characterization result was shown in FIG. 1. FIG. 1 aberration-corrected scanning transmission electron microscopy images of the fresh catalyst, in which, FIG. a shows the single-atom sites state of metal (part of it is cycled by dashed line) and FIG. b shows the existence of clusters or nanoparticles of metal in the catalyst. It can be seen that there are a

TABLE 2

The treatment conditions and performance comparison of Examples 21 to 35.

| | | Treatment conditions | | | Optimal performance | |
|---|---|---|---|---|---|---|
| Example | Catalyst composition | Atmosphere and Concentration | Time (min) | Temperature (° C.) | Conversion (%) | Selectivity (%) |
| EX21 | $Pt_{(0.3\ wt\ \%)}Zn_{(1\ wt\ \%)}/Al_2O_3$ | 4% ethylenediamine | 30 | 500 | 20.78 | 82.92 |
| EX22 | $Cr_{(0.5\ wt\ \%)}Zn_{(1.5\ wt\ \%)}/Al_2O_3$ (200713a) | 4% ethylenediamine | 30 | 500 | 23.1 | 84.9 |
| EX23 | $Mn_{(0.5\ wt\ \%)}Zn_{(1.5\ wt\ \%)}/Al_2O_3$ (d200829a) | 4% ethylenediamine | 30 | 500 | 14.2 | 82.2 |
| EX24 | $Fe_{(0.5\ wt\ \%)}Zn_{(1.5\ wt\ \%)}/Al_2O_3$ (200713b) | 4% ethylenediamine | 30 | 500 | 16 | 83.6 |
| EX25 | $Co_{(0.5\ wt\ \%)}Zn_{(1.5\ wt\ \%)}/Al_2O_3$ (200918a) | 4% ethylenediamine | 30 | 500 | 19.9 | 84.6 |
| EX26 | $Ni_{(0.5\ wt\ \%)}Zn_{(1.5\ wt\ \%)}/Al_2O_3$ (200918b) | 4% ethylenediamine | 30 | 500 | 21 | 71.3 |
| EX27 | $Cu_{(0.5\ wt\ \%)}Zn_{(1.5\ wt\ \%)}/Al_2O_3$ (d200730) | 4% ethylenediamine | 30 | 500 | 15.9 | 82.2 |
| EX28 | $La_{(0.5\ wt\ \%)}Zn_{(1.5\ wt\ \%)}/Al_2O_3$ (d200829b) | 4% ethylenediamine | 30 | 500 | 14.1 | 82.6 |
| EX29 | $Ir_{(0.1\ wt\ \%)}Co_{(0.5\ wt\ \%)}Zn_{(1\ wt\ \%)}/Al_2O_3$ (200608b) | 4% ethylenediamine | 36 | 500 | 41.288 | 92.0325 |
| EX30 | $Ir_{(0.1\ wt\ \%)}Co_{(0.75\ wt\ \%)}Zn_{(0.7\ wt\ \%)}/Al_2O_3$ (200608c) | 4% ethylenediamine | 30 | 500 | 38.656 | 92.22 |
| EX31 | $Ir_{(0.1\ wt\ \%)}Co_{(1.5\ wt\ \%)}/Al_2O_3$ | 4% ethylenediamine | 30 | 500 | 37.88 | 91.92 |
| EX32 | $Ir_{(0.1\ wt\ \%)}Zn_{(1.5\ wt\ \%)}Al_{(1.24\ wt\ \%)}/Al_2O_3$ | 4% ethylenediamine | 30 | 500 | 28.34 | 92.5 |
| EX33 | $Ir_{(0.15\ wt\ \%)}Zn_{(1.5\ wt\ \%)}Al_{(1.24\ wt\ \%)}/Al_2O_3$ | 4% ethylenediamine | 30 | 500 | 32.73 | 93.39 |
| EX34 | $Ir_{(0.15\ wt\ \%)}Zn_{(1.5\ wt\ \%)}/NaY$ | 4% ethylenediamine | 30 | 500 | 16.06 | 67 |
| EX35 | $Ir_{(0.3\ wt\ \%)}Zn_{(3\ wt\ \%)}/SiO_2$ | 4% ethylenediamine | 30 | 500 | 13.26 | 76.72 |

The test results in Table 2 show that the catalysts prepared using Zn, Co or Al as promoter possess good catalytic activity for dehydrogenation of alkane, whether the active metal is noble metal or transition metal. The catalytic activity of noble metal is higher than that of transition metal 3. Regeneration of Catalyst Example 36 reveals that the regeneration method of catalyst in this invention is simple and efficient After regeneration, the catalytic performance of the catalyst does not obviously decrease Under the same test conditions (hydrogen to hydrocarbon ratio is 0.25), the conversion and selectivity of the regeneration catalyst were comparable to those of the fresh catalyst.

In fact, the inventors regenerated the catalyst for 50 times, and the resulting catalyst still has high conversion and high selectivity.

It should be noted that the test conditions used in Example 36 were slightly different from those in other examples, in which a certain proportion of hydrogen was mixed with propane gas to simulate the actual operating conditions of industrial production.

4. Structure Characterization of Catalysts.

The inventors characterized the structure of fresh catalyst without carbon and nitrogen (CN) treatment, where the large amount of metal dispersed in the single-atom sites state, as well as metal in clusters state even in nanoparticles state in the catalyst. However, the method of the present invention is effective for improving the conversion and selectivity of the above catalyst.

Figure 2:
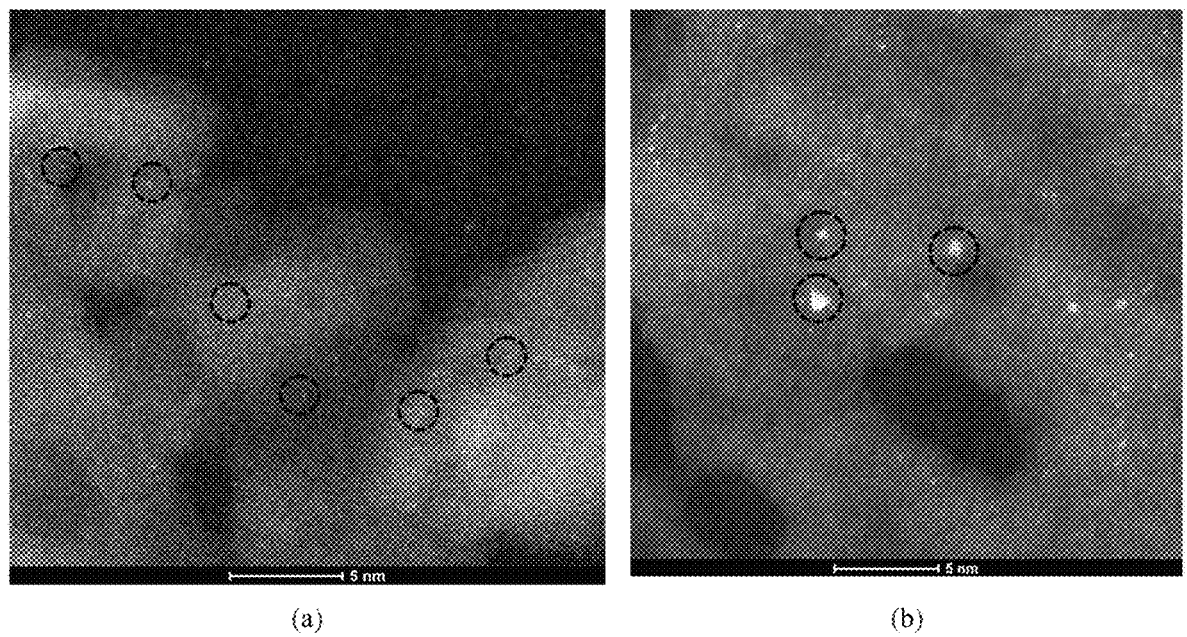
FIG. 2 shows aberration-corrected scanning transmission electron microscopy images of the catalyst regenerated for 50 times, in which (a) shows the metal in the single-atom sites state (part of it is cycled by dashed line); (b) shows the existence of clusters or nanoparticles of metal in the catalyst.

FIG. 2 shows Aberration-corrected Scanning Transmission Electron microscopy images of the catalyst regenerated by burning coke for 50 times. The catalyst composition is the same as that of FIG. 1. In FIG. 2. FIG. a shows the single-atom sites state of metal (part of it is cycled by dashed line) and FIG. b shows the existence of clusters or nanoparticles of metal in the catalyst. It is also revealed that the active metal also exists in three states of single-atom sites, clusters and nanoparticles in the catalyst after repeated regeneration, and the method of this invention is also effective.

Example 37

This example provided a single-atom catalyst for dehydrogenation of propane. The catalyst uses alumina spheres with diameter of 1-2 mm as support, Ir as active component, Sn as first promoter and K as second promoter. In the catalyst, the mass percentage content of Ir is 0.3%, the mass percentage content of the first promoter is 1.0% s, and the percentage content of the second promoter is 1.0% The catalyst was prepared by isovolumetric impregnation method and treatment with ethylenediamine gas to load single atoms of Ir. The specific process was as follows: 5 g of alumina spheres (diameter of 1 mm to 2 mm, specific surface area of 220 $m^2/g$, water absorption rate of 0.442) were weighed. 2.21 mL of mixed impregnation solution of $H_2IrCl_6$, $SnCl_4$, HCl and KCl was prepared according to 0.3 wt % of active component Ir, 1.0 wt % of promoter Sn and 1.0 wt % of K based on the catalyst weight. The prepared solution was added dropwise into the alumina spheres. The mixture system was aged for 4 h. dried at 80° C. for 8 h. then calcined at 600° C. for 4 h, and then activated for 0.5 h using a mixture gas of ethylenediamine and nitrogen with a volume ratio of 1:24, cooled to room temperature naturally, to obtain the catalyst C-1.

Example 38

This example provided a single-atom catalyst for dehydrogenation of propane. The catalyst uses spherical alumina with diameter of 1-2 mm as support, Ir as active component, Zn as a first promoter and K as a second promoter. In the catalyst, the mass percentage content of Ir is 0.3%, the mass percentage content of the first promoter is 1.0%, and the percentage content of the second promoter is 1.0%. The catalyst was prepared by isovolumetric impregnation method and treatment with ethylenediamine gas to load Ir single atoms. The specific process was as follows' 5 g of alumina spheres (diameter of 1 mm to 2 mm, specific surface area of 220 $m^2/g$, water absorption rate of 0.442) were weighed. 2.21 mL of mixed impregnation solution of $H_2IrCl_6$, $Zn(NO_3)_2$, HCl and KCl was prepared according to 0.3 wt % of active component Ir, 1.0 wt % of promoter Zn and 1.0 wt % of K based on the catalyst weight. The prepared solution was added dropwise into the alumina spheres. The mixture system was aged for 4 h, dried at 80° C. for 8 h, then calcined at 600° C. for 4 h, and then activated for 0.5 h using a mixture gas of ethylenediamine and nitrogen with a volume ratio of 1:24, cooled to room temperature naturally, to obtained the catalyst C-2.

Example 39

This example provided a single-atom catalyst for dehydrogenation of propane. The catalyst uses spherical alumina with diameter of 1-2 mm as support, Ir as active component, Sn as a first promoter and Na as a second promoter. In the catalyst, the mass percentage content of Ir is 0.3%, the mass percentage content of the first promoter is 1.0%, and the percentage content of the second promoter is 1.0%. The catalyst was prepared by isovolumetric impregnation method and treatment with ethylenediamine gas to load Ir single atoms. The specific process was as follows: 5 g of alumina spheres (diameter of 1 mm to 2 mm, specific surface area of 220 $m^2/g$, water absorption rate of 0.442) were weighed. 2.21 mL of mixed impregnation solution of $H_2IrCl_6$, $SnCl_4$, HCl and NaCl was prepared according to 0.3 wt % of active component Ir, 1.0 wt % of promoter Sn and 10 wt % of Na based on the catalyst weight. The prepared solution was added dropwise into the alumina spheres. The mixture system was aged for 4 h, dried at 80° C. for 8 h. then calcined at 600° C. for 4 h. and then activated for 0.5 h using a mixture gas of ethylenediamine and nitrogen with a volume ratio of 1:24, and cooled to room temperature naturally, to obtain the catalyst C-3.

Example 40

This example provided a single-atom catalyst for dehydrogenation of propane. The catalyst uses alumina spheres with diameter of 1-2 mm as support, Ir as active component, Zn as a first promoter and Na as a second promoter. In the catalyst, the mass percentage content of Ir is 0.3%, the mass percentage content of the first promoter is 1.0/6, and the percentage content of the second promoter is 1.0%. The catalyst was prepared by isovolumetric impregnation method and treatment with ethylenediamine gas to load Ir single atoms. The specific process was as follows: 5 g of alumina spheres (diameter of 1 mm to 2 mm, specific surface area of 220 $m^2/g$, water absorption rate of 0.442) were weighed. 2.21 mL of mixed impregnation solution of $H_2IrCl_6$, $Zn(NO_3)_2$, HCl and NaCl was prepared according to 0.3 wt % of active component Ir, 1.0 wt % of promoter Zn and 1.0 wt % of Na based on the catalyst weight. The prepared solution was added dropwise into the alumina spheres. The mixture system was aged for 4 h, dried at 80° C. for 8 h, then calcined at 600° C. for 4 h. and then activated for 0.5 h using a mixture gas of ethylenediamine and nitrogen with a volume ratio of 1:24, cooled to room temperature naturally, to obtain the catalyst C-4.

Comparative Example 2

This comparative example provided a catalyst for dehydrogenation of propane. The catalyst uses alumina spheres with diameter of 1-2 mm as support and Ir as active component, without any other promotor. The mass percentage content of Ir in the catalyst is 0.3%. The catalyst was prepared by isovolumetric impregnation method. The specific process was as follows: 5 g of alumina spheres (diameter of 1 mm to 2 mm, specific surface area of 220 $m^2/g$, water absorption rate of 0.442) were weighed. 2.21 mL of impregnation solution of $H_2IrCl_6$ and HCl was prepared according to 0.3 wt % of active component Ir based on the catalyst weight. The prepared solution was added dropwise into the alumina spheres. The mixture system was aged for 4 h, dried at 80° C. for 8 h, then calcined at 600° C. for 4 h. and then activated for 0.5 h using a mixture gas of ethylenediamine and nitrogen with a volume ratio of 1:24, then cooled to room temperature naturally, to obtain the catalyst D-1.

Comparative Example 3

This comparative example provided a catalyst for dehydrogenation of propane. The catalyst uses alumina spheres with diameter of 1-2 mm as support, Ir as active component and Sn as promoter. In the catalyst, the mass percentage content of Ir is 0.3% and the mass percentage content of Sn is 1.0% The catalyst was prepared by isovolumetric impregnation method. The specific process was as follows: 5 g of alumina spheres (diameter of 1 mm to 2 mm, specific surface area of 220 $m^2/g$, water absorption rate of 0.442) were weighed. 2.21 mL of impregnation solution of $H_2IrCl_6$, $SnCl_4$ and HCl was prepared according to 0.3 wt % of active component Ir and 1.0 wt % of promoter Sn based on the catalyst weight. The prepared solution was added dropwise into the alumina spheres. The mixture system was aged for 4 h. dried at 80° C. for 8 h. then calcined at 600° C. for 4 h., and then activated for 0.5 h using a mixture gas of ethylenediamine and nitrogen with a volume ratio of 1:24, then cooled to room temperature naturally, to obtain the catalyst D-2.

Comparative Example 4

This comparative example provided a catalyst for dehydrogenation of propane. The catalyst uses alumina spheres with diameter of 1-2 mm as support. Ir as active component and Zn as promoter. In the catalyst, the mass percentage content of Ir is 0.3% and the mass percentage content of Zn is 1.0%. The catalyst was prepared by isovolumetric impregnation method. The specific process was as follows: 5 g of alumina spheres (diameter of 1 mm to 2 mm, specific surface area of 220 m$^2$/g, water absorption rate of 0.442) were weighed. 2.21 mL of impregnation solution of $H_2IrCl_6$, $Zn(NO_3)_2$ and HCl was prepared according to 0.3 wt % of active component Ir and 1.0 wt % of promoter Zn based on the catalyst weight. The prepared solution was added dropwise into the alumina spheres. The mixture system was aged for 4 h. dried at 80° C. for 8 h. then calcined at 600° C. for 4 h, and then activated for 0.5 h using a mixture gas of ethylenediamine and nitrogen with a volume ratio of 1:24, then cooled to room temperature naturally, to obtain the catalyst D-3.

Regeneration Example 41

The deactivated catalyst of example 37-4 after reaction was calcined at 400° C. for 3 h under air atmosphere to remove coke. Then the obtained regenerated sample was treated at 500° C. for 30 min under an atmosphere of the mixture gas of ethylenediamine and nitrogen with a volume ratio of 1:24.

The regenerated catalyst was evaluated by dehydrogenation of propane to propylene. It is found that compared with a fresh catalyst, the regenerated catalyst possesses similar conversion and selectivity Method for Catalytic Activity Test and the Test Result The catalysts of examples 37-40 and comparative examples 2-4 of this invention were used to catalyze the dehydrogenation of propane to propylene, the specific method was as follows: 1.0 g of catalyst was placed in a fixed bed reactor for the dehydrogenation of propane to propylene; under normal pressure condition, nitrogen was introduced to the reaction system at a flow rate of 13.1 mL/min; and the temperature of the reaction system was raised from room temperature to 600° C. at a rate of 3° C./min. Then a mixture gas of hydrogen and propane with a volume ratio of 1.2 was introduced to the reaction system at a total flow rate of 39.3 mL/min, to dehydrogenate propane to propylene under normal pressure. The catalytic performances of the catalysts of examples 37-40 and comparative examples 2-4 in this invention for dehydrogenation of propane to propylene are shown in Table 3.

TABLE 3

Catalytic performances of the catalysts of examples 37-40 and comparative examples 2-4 for dehydrogenation of propane to propylene

| catalyst | Active components of catalyst (based on alumina support) | Conversion (1 h) | Selectivity (1 h) | Conversion (2 h) | Selectivity (2 h) |
|---|---|---|---|---|---|
| C-1 | Ir0.3% Sn1% K1% | 33.99% | 94.88% | 34.16% | 94.60% |
| C-2 | Ir0.3% Zn1% K1% | 35.69% | 94.59% | 35.74% | 94.54% |
| C-3 | Ir0.3% Sn1% Na1% | 35.31% | 94.45% | 34.92% | 94.30% |
| C-4 | Ir0.3% Zn1% Na1% | 33.56% | 94.03% | 33.42% | 93.86% |
| D-1 | Ir0.3% | 27.82% | 93.21% | 27.13% | 93.02% |
| D-2 | Ir0.3% Sn1% | 33.51% | 93.11% | 29.62% | 92.87% |
| D-3 | Ir0.3% Zn1% | 33.04% | 92.90% | 33.31% | 93.10% |

The Table 3 shows that the addition of the first promoter and/or the second promoter improves the conversion and selectivity of the catalyst obviously. In addition, the performance data of 2 h reveals that the catalyst of this invention exhibits a better stability.

The above examples only clearly illustrate the present invention, but are not to be construed as limiting the present invention. To common technician of related field, other different forms of variations or adjustments can be further made on the basis of the illustration above. It is impossible to exhaustively describe all the possible situation here, but the obvious variations or adjustments extended from the technical solution of the present invention are still within the protection scope of this invention.

What is claimed is:

1. A method for treating metallic catalyst comprising: treating metal supported catalyst with ammonia or nitrogen-containing organic at 10° C.-700° C., the metal supported catalyst is a $M_a$-$M_b$-$M_c$ metal supported catalyst, wherein $M_a$ is active metal which is selected from one or more of noble metal and transition metal, wherein the noble metal is selected from one or more mixtures of Pt, Au, Ru, Rh, Pd, Ir and Ag, the transition metal is selected from La, Fe, Co, Mn, Cr, Ni and Cu, the content of $M_a$ is 0.01-5 wt % based on catalyst weight; $M_b$ is selected from one or more combinations of Zn, Sn, Co and Al, the content of $M_b$ is 0.1-20 wt % based on catalyst weight; $M_c$ is selected from K, Na and a mixture thereof, the content of $M_c$ is 0-2.0 wt %, and a support of the metal supported catalyst comprises alumina, silica-alumina, zirconia, cerium oxide, titanium oxide, or molecular sieves or the mixture thereof.

2. The method according to claim 1, wherein the metal supported catalyst does not contain $M_c$, wherein $M_a$ is Pt, Ru, Pd, Ir, Cr, Ni, PtPd, IrPt, IrPd, or IrPtPd; $M_b$ is Zn, Co or Zn—Co mixture; the support is commonly used in industry, which comprises alumina, silica-alumina, zirconia, cerium oxide, titanium oxide, or molecular sieves or the mixture thereof; alternatively, the support is γ-alumina, titanium oxide, silica, NaY molecular sieve supports; a shape of the support is selected from non-formed powder, and shaped structure; the shaped structure is selected from spherical shape, strip shape, cylindrical shape, shape with multi-porous channels, honeycomb shape.

3. The method according to claim 2, wherein the $M_a$ metal is loaded on the support in a state of single-atom sites, or in a state of coexistence of single-atom sites with clusters and/or nanoparticles; alternatively, the $M_a$ metal is loaded on the support in the state of single-atom sites, or in the state of coexistence of single-atom sites and clusters, or in the state of coexistence of single-atom sites, clusters and nanoparticles; the content of $M_a$ is 0.01-5 wt % or 0.05-2 wt % based on catalyst weight; the content of $M_b$ is 0.1-20 wt %, 0.1-10 wt %, or 0.5-4 wt % based on catalyst weight.

4. The method according to claim 3, wherein the metal supported catalyst is prepared by loading a $M_a$ metal precursor and a $M_b$ precursor on the support; the loading of $M_a$ and $M_b$ metal is carried out simultaneously or sequentially.

5. The method according to claim 2, wherein the ammonia comprises ammonia gas or substance that can release ammonia; the nitrogen-containing organic is selected from $C_{1-6}$ alkyl amine, $C_{2-6}$ alkenyl amine, $C_{6-20}$ aryl amine, $C_{4-20}$ cyclic alkyl amine, $C_{4-20}$ nitrogen-containing heterocyclic ring, $C_{4-20}$ nitrogen-containing heteroaromatic ring and $(RCO)_xNR_{3-x}$, wherein R is H or $C_{1-6}$ alkyl, x is 1 or 2; the amine is monamine or polyamine; alternatively, the alkyl, alkenyl, aryl, nitrogen-containing heterocycle ring and nitrogen-containing heteroaromatic ring are independently further substituted by oxygen, carbonyl, carboxyl, ester group, or amino group; the aryl is monocyclic aryl or fused polycyclic aryl; the nitrogen-containing heterocyclic ring is monocyclic or fused non-aromatic ring containing cyclic nitrogen atom, and a cyclic carbon atom is optionally replaced by oxygen; the nitrogen-containing heteroaromatic ring is monocyclic or fused polycyclic heteroaromatic ring containing cyclic nitrogen atom, and a cyclic carbon atom is optionally replaced by oxygen; alternatively, the nitrogen-containing organic is selected from $C_{1-6}$ alkyl amine, $C_{1-6}$ alkyl diamine, $C_{6-20}$ aryl amine, dimethyl formamide; alternatively, the nitrogen-containing organic is selected from ethylenediamine, triethylamine, butylamine, aniline and dimethyl formamide; alternatively, the nitrogen-containing organic is ethylenediamine.

6. The method according to claim 2, treating the metal supported catalyst with ammonia or gaseous nitrogen-containing organic, or treating metal supported catalyst with $NH_3$ gas, nitrogen-diluted $NH_3$ gas, nitrogen-diluted gaseous nitrogen-containing organic; the treatment temperature is in the range of 10° C. to 700° C., or in the range of 300° C. to 600° C.; the treatment time is 1-400 min, or 5-150 min.

7. The method according to claim 1, wherein $M_a$ is Ir, $M_b$ is selected from Zn, Sn and mixture thereof, $M_c$ is selected from K, Na and mixture thereof, the content of $M_a$ is 0.1-2 wt % based on catalyst weight, the content of $M_b$ is 0.1-3.0 wt % based on catalyst weight, the content of $M_c$ is 0.1-2.0 wt % based on catalyst weight; the support is alumina support, or shaped alumina support; the $M_a$ metal is dispersed and loaded on the support in a state of single-atom sites, or clusters, or nanoparticles; alternatively, the $M_a$ metal is loaded on the support in a state of single-atom sites, or in the state of coexistence of single-atom sites with clusters and/or nanoparticles;

wherein the ammonia comprises ammonia gas or substance that can release ammonia; the nitrogen-containing organic is selected from $C_{1-6}$ alkyl amine, $C_{2-6}$ alkenyl amine, $C_{6-20}$ aryl amine, $C_{4-20}$ cyclic alkyl amine, $C_{4-20}$ nitrogen-containing heterocyclic ring, $C_{4-20}$ nitrogen-containing heteroaromatic ring and $(RCO)_xNR_{3-x}$, wherein R is H or $C_{1-6}$ alkyl, X is 1 or 2; the amine is a monamine or polyamine; optionally, the alkyl, alkenyl, aryl, nitrogen-containing heterocycle ring, nitrogen-containing heteroaromatic ring are independently further substituted by oxygen, carbonyl, carboxyl, ester group, or amino group; the aryl is monocyclic aryl or fused polycyclic aryl; the nitrogen-containing heterocyclic ring is monocyclic or fused non-aromatic ring containing cyclic nitrogen atom, and a cyclic carbon atom is optionally replaced by oxygen; the nitrogen-containing heteroaromatic ring is monocyclic or fused polycyclic heteroaromatic ring containing cyclic nitrogen atom, and a cyclic carbon atom is optionally replaced by oxygen.

8. The method according to claim 7, wherein a preparation method of a catalyst precursor is loading a $M_a$ metal precursor, a $M_b$ precursor and a $M_c$ precursor on the support to form the catalyst precursor, the $M_a$ metal precursor is soluble inorganic salt, organic salt or metal complex of $M_a$ metal in a solvent, alternatively the $M_a$ metal precursor is nitrate, chloride, sulphate, acetate, acetylacetone salt, complex; the $M_b$ or $M_c$ metal precursor is soluble organic or inorganic salt of $M_b$ or $M_c$ in a solvent, alternatively the $M_b$ and $M_c$ metal precursor is nitrate, chloride, sulphate, acetate, oxalate, acetylacetone salt; the solvent is water or alcohol, wherein the alcohol is methanol or ethanol.

9. The method according to claim 8, wherein the preparation method of the catalyst precursor comprises, optionally, aging at the range of room temperature to 80° C., the aging time is 0.5-40 h, or 2-8 h; optionally, after aging, drying at 60-150° C., or 80-120° C. the drying time is 2-20 h, or 6-10 h; calcining the dried catalyst at 400-600° C., the calcining time is 3-6 h, to obtain the catalyst precursor.

10. The method according to claim 7, wherein the ammonia is ammonia gas, the nitrogen-containing organic is alternatively ethylenediamine, triethylamine, butylamine, aniline or dimethyl formamide.

11. The method according claim 7, wherein the treating is performed by using gaseous ethylenediamine at 300-600° C., the gaseous ethylenediamine is optionally the mixture of ethylenediamine and nitrogen in a volume ratio of 1-5:20-24, the treating time is 0.05-4 h, or 0.5-1.5 h.

12. The method according to claim 7, wherein the catalyst is $Ir/Zn/K@Al_2O_3$, $Ir/Sn/K@Al_2O_3$, $Ir/Zn/Na@Al_2O_3$, $Ir/Sn/Na@Al_2O_3$, wherein the content of Ir is 0.1-2 wt % based on catalyst weight, the content of Zn or Sn is 0.1-3.0 wt % based on catalyst weight, and the content of K or Na is 0.1-2.0 wt % based on catalyst weight.

13. A method for preparing light olefin by the dehydrogenation of light alkane, comprising: using a catalyst to catalyze the dehydrogenation of $C_{2-6}$ alkane to obtain $C_{2-6}$ olefin, wherein the catalyst is obtained by the method according to claim 1.

14. A regeneration method of metal supported catalyst, the metal supported catalyst is a $M_a$-$M_b$-$M_c$ metal supported catalyst, wherein the metal supported catalyst does not contain $M_c$ metal, the method comprising:

step A, removing substances which cause the metal supported catalyst poisoned or deactivated to regenerate the metal supported catalyst;

step B, treating the catalyst obtained from step A by ammonia or a nitrogen-containing organic at 10-700° C. to obtain an activated catalyst;

in the step A, the substances which cause the catalyst deactivated comprise coke and/or sulfur; the removing comprises: oxidation removing by $O_2$, oxidation removing by air, or reduction removing by $H_2$;

wherein $M_a$ metal is an active metal which is selected from one or more of noble metal and transition metal, wherein the noble metal is selected from one or more mixtures of Pt, Au, Ru, Rh, Pd, Ir and Ag, the transition metal is selected from La, Fe, Co, Mn, Cr, Ni or Cu; alternatively, the active metal is Pt, Ru, Pd, Ir, Cr, Ni, PtPd, IrPt, IrPd, or IrPtPd; $M_b$ metal is selected from one or more combinations of Zn, Co and Al, alternatively $M_b$ metal is Zn, Co or Zn—Co mixed metal;

the support is selected from alumina, silica-alumina, zirconia, cerium oxide, titanium oxide, or molecular sieve or the mixture thereof; alternatively the support is γ-alumina, titanium oxide, silica or NaY molecular sieve;

the $M_a$ metal is loaded on the support in a state of single-atom sites, or in a state of coexistence of single-atom sites with clusters and/or nanoparticles; alternatively, the $M_a$ metal is loaded on the support in the state of single-atom sites, or in the state of coexistence of single-atom sites and clusters, or in the state of coexistence of single-atom sites, clusters and nanoparticles; the content of $M_a$ is 0.01-5 wt %, or 0.05-2 wt % based on catalyst weight; the content of $M_b$ is 0.1-20 wt %, 0.1-10 wt %, or 0.5-4 wt % based on catalyst weight;

the nitrogen-containing organic is selected from $C_{1-6}$ alkyl amines, $C_{2-6}$ alkenyl amine, $C_{6-20}$ aryl amine, $C_{4-20}$ cyclic alkyl amine, $C_{4-20}$ nitrogen-containing heterocyclic ring, $C_{4-20}$ nitrogen-containing heteroaromatic ring and $(RCO)_xNR_{3-x}$, wherein R is H or $C_{1-6}$ alkyl, x is 1 or 2; the amine is a monamine or polyamine; optionally, the alkyl, alkenyl, aryl, nitrogen-containing heterocycle ring, and nitrogen-containing heteroaromatic ring are independently further substituted by oxygen, carbonyl, carboxyl, ester group, or amino group; the aryl is monocyclic aryl or fused polycyclic aryl; the nitrogen-containing heterocyclic ring is a monocyclic or fused non-aromatic ring containing cyclic nitrogen atom, and a cyclic carbon atom is optionally replaced by oxygen; the nitrogen-containing heteroaromatic ring is a monocyclic or fused polycyclic heteroaromatic ring containing cyclic nitrogen atom, and a cyclic carbon is optionally replaced by oxygen; alternatively, the nitrogen-containing organic is $C_{1-6}$ alkyl amine, $C_{1-6}$ alkyl diamine, $C_{6-20}$ aryl amine, dimethyl formamide.

15. The regeneration method according to claim 13, wherein $M_a$ is one or more mixtures of Pt, Ru, Ir and Au: $M_b$ is Zn; the support is alternatively alumina; the nitrogen-containing organic is ethylenediamine, triethylamine, butylamine, aniline or dimethyl formamide.

16. A method for preparing light olefin by the dehydrogenation of light alkane, comprising: using a catalyst to catalyze the dehydrogenation of $C_{2-6}$ alkane to obtain $C_{2-6}$ olefin, wherein the catalyst is obtained by the regeneration method according to claim 14.

17. A regeneration method of $M_a$-$M_b$-$M_c$ metal supported catalyst, comprising:

step A, removing substances which cause the $M_a$-$M_b$-$M_c$ metal supported catalyst to be poisoned or deactivated to regenerate the catalyst;

step B, treating the catalyst with ammonia or nitrogen-containing organic in the range of room temperature to 700° C. to obtain an activated catalyst;

wherein $M_a$ is Ir, $M_b$ is selected from Zn, Sn and the mixture of both, $M_c$ is selected from K, Na or the mixture of both, the content of $M_a$ is 0.1-2 wt % based on catalyst weight, the content of the $M_b$ is 0.1-3.0 wt % based on catalyst weight, the content of the $M_c$ is 0.1-2.0 wt % based on catalyst weight, a support of the $M_a$-$M_b$-$M_c$ metal supported catalyst is alumina, or shaped alumina support; the $M_a$ metal is dispersed and loaded on the support in a state of single-atom sites, clusters or nanoparticles; alternatively $M_a$ metal is dispersed and loaded on the support in the state of single-atom sites, or in the state of coexistence of single-atom sites with clusters and/or nanoparticles;

in the step A, the substances which cause the $M_a$-$M_b$-$M_c$ metal supported catalyst poisoned or deactivated comprise coke and/or sulfur; the removing comprises: oxidation removing by $O_2$, oxidation removing by air, or reduction removing by $H_2$;

in the step B, treating the catalyst by ammonia or nitrogen-containing organic, wherein the nitrogen-containing organic is optionally selected from ethylenediamine, triethylamine, butylamine, aniline and dimethyl formamide, the treatment temperature is optionally 300-700° C.

18. The regeneration method according to claim 17, wherein; in the step B, in the range of 400-600° C., treating the catalyst by gaseous ethylenediamine, or by the mixture of ethylenediamine and nitrogen in a volume ratio of 1-5: 20-24.

19. A method for preparing light olefin by the dehydrogenation of light alkane, comprising: using a catalyst to catalyze the dehydrogenation of $C_{2-6}$ alkane to obtain $C_{2-6}$ olefin, wherein the catalyst is obtained by the regeneration method according to claim 17.

* * * * *